United States Patent [19]

Rossiter

[11] Patent Number: 5,223,716
[45] Date of Patent: Jun. 29, 1993

[54] METHOD OF AND MEANS FOR EXTENDING THE HIGH TEMPERATURE/HIGH PRESSURE OPERATING RANGE OF OPTICAL ELEMENTS

[76] Inventor: Valentine J. Rossiter, Oakenlawn House, Enniskerry, Co. Wicklow, Dublin, Ireland

[21] Appl. No.: 865,232

[22] Filed: Apr. 8, 1992

[30] Foreign Application Priority Data

Apr. 17, 1991 [GB] United Kingdom ............... 9108195

[51] Int. Cl.⁵ ...................... G01N 21/03; G01N 21/05
[52] U.S. Cl. ................................... 250/343; 356/246
[58] Field of Search ............... 250/343, 339, 373; 356/246, 244

[56] References Cited

U.S. PATENT DOCUMENTS

| | | | |
|---|---|---|---|
| 3,886,364 | 5/1975 | Walker et al. | 250/343 |
| 4,614,428 | 9/1986 | Harris et al. | 356/246 |
| 4,822,166 | 4/1989 | Rossiter | 356/246 |
| 5,003,174 | 3/1991 | Dätwyler et al. | 250/343 |
| 5,054,919 | 10/1991 | Bryan | 356/246 |
| 5,120,129 | 6/1992 | Farquharson et al. | 356/246 |
| 5,124,555 | 6/1992 | Härtl | 250/343 X |

FOREIGN PATENT DOCUMENTS

| | | | |
|---|---|---|---|
| 3305982 | 8/1984 | Fed. Rep. of Germany | 356/246 |
| 58-111742 | 7/1983 | Japan | 356/246 |

Primary Examiner—Constantine Hannaher
Assistant Examiner—Edward J. Glick
Attorney, Agent, or Firm—Sughrue, Mion, Zinn, Macpeak & Seas

[57] ABSTRACT

A method is provided to extend the high temperature and/or high pressure operating range of a primary radiation-transmitting element 5,6 by the addition of a secondary enclosure 15,16 for containing a pressurized gas atmosphere and a secondary radiation-transmitting element 23,24 wherein the primary radiation-transmitting element 5,6 experiences a reduced pressure differential.

9 Claims, 3 Drawing Sheets

METHOD OF AND MEANS FOR EXTENDING THE HIGH TEMPERATURE/HIGH PRESSURE OPERATING RANGE OF OPTICAL ELEMENTS

BACKGROUND OF THE INVENTION

1. Field of the Invention

This invention relates to a method and means for extending the operating temperature range of spectroscopic window materials which are used to contain fluids at high pressures. The invention may be applied to any type of optical element exposed to such operating conditions.

2. Background

In general, the mechanical hardness and the mechanical strength of materials is reduced at elevated temperatures. In spectroscopy, where it are required to examine a fluid sample (for example, a liquid, gas or supercritical fluid) under high pressure and high temperature, the fluid must be contained in a vessel with at least one optically transmitting element which retains the fluid. Generally, this optical element becomes the limiting factor for both the pressure and temperature range of the vessel because of the lower mechanical strength of optical materials in comparison to metals. In many cases, the element is a disc-shaped window, though many other forms may be used, such as a lens, a multiple internal reflection element, an optic fibre, etc. In the case of a disc shaped-window, the dimensions of the disc (particularly the thickness and unsupported area) are chosen in relation to the pressure it is required to bear considering the mechanical strength of the optical material of the disc and allowing a substantial safety factor (often four-fold) in the calculations. Materials such as zinc sulphide (ZnS) and zinc selenide (ZnSe) are often preferred because of the spectral range over which they transmit in the infrared region and because their useful mechanical strength means they are suitable for high pressure applications. However, at elevated temperatures (say above 100° C.) the pressure rating of such windows must be reduced as a consequence of their loss in mechanical strength. The behaviour of such windows may also be unpredictable under these high temperature and high pressure operating conditions; failure may be catastrophic, possibly with the window disintegrating forming dangerous splinters which may be ejected from the system with explosive force. This invention addresses these and other problems and shows how the operating pressure/temperature range may be extended with much improved safety. Pressures of the order of 7MPa to 30MPa are commonly of interest in industry. This invention is not restricted t this pressure range but does overcome the problem of providing satisfactory optical elements for use in chemical and related industries.

SUMMARY OF THE INVENTION

According to one aspect of the invention, there is provided means for supporting a primary optical element which is subject to high temperatures and high pressures, comprising a secondary enclosure for containing a pressurized gas atmosphere and which incorporates a secondary optical element, wherein the primary optical element experiences a reduced pressure differential.

Preferably the pressure differential experienced by the primary optical element is near zero.

The secondary optical element may be operated at a temperature which is lower than that of the primary optical element and which preferably, is the temperature at which the secondary optical element has optimal mechanical strength The secondary optical element may be refrigerated and operated at below ambient temperature.

The pressure limitation on the system is then determined by the secondary optical element, essentially irrespective of the operating temperature of the primary optical element. By way of illustration, embodiments of the invention will now be described in detail.

BRIEF DESCRIPTION OF THE DRAWINGS

FIGS. 2A, 2B, 2C, 2D and 2E illustrate a second embodiment of the invention wherein FIG. 2A is a cross-sectional view, FIG. 2B is an end view of the device, FIG. 2C is an end view of the entire device, FIG. 2D is an end view of a cell portion of the device, and FIG. 2E is an end view of the optical portion of the device.

DETAILED DESCRIPTION OF A PREFERRED EMBODIMENT OF THE INVENTION

Figure 1A:
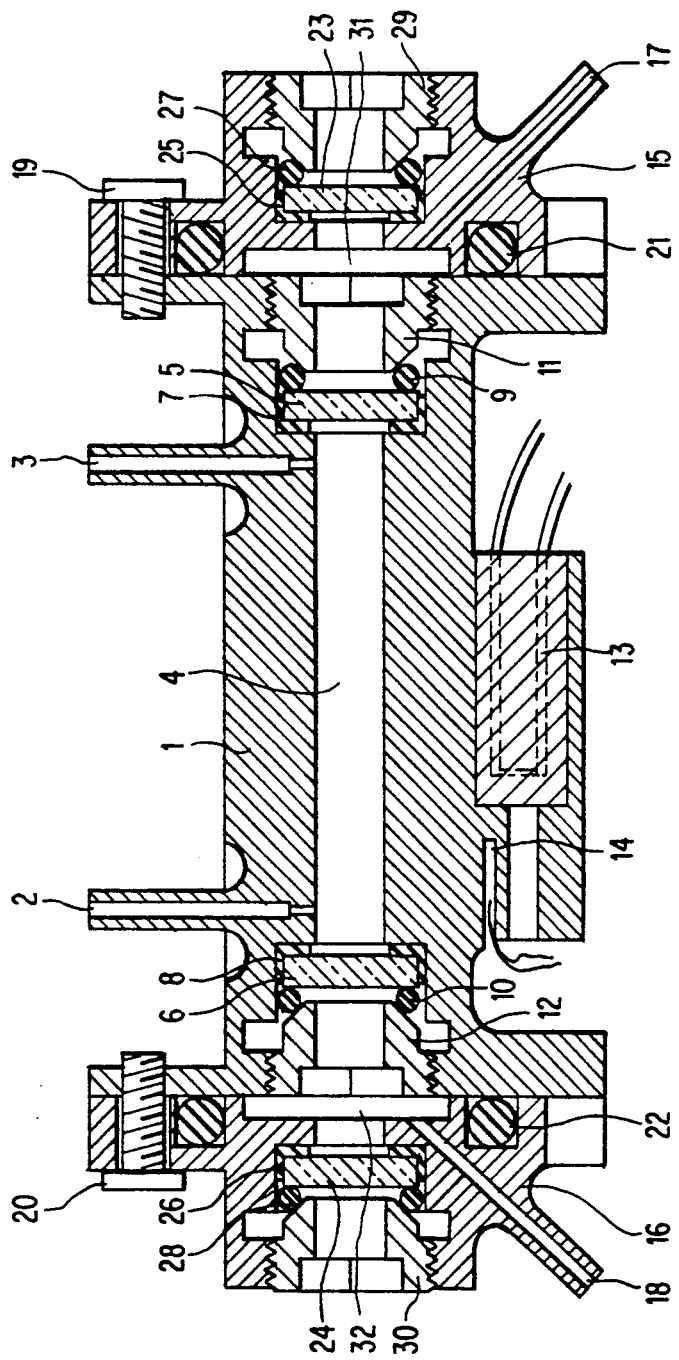
FIGS. 1A and 1B are respectively cross-sectional and end views of a first embodiment of the present invention.
Figure 1B:
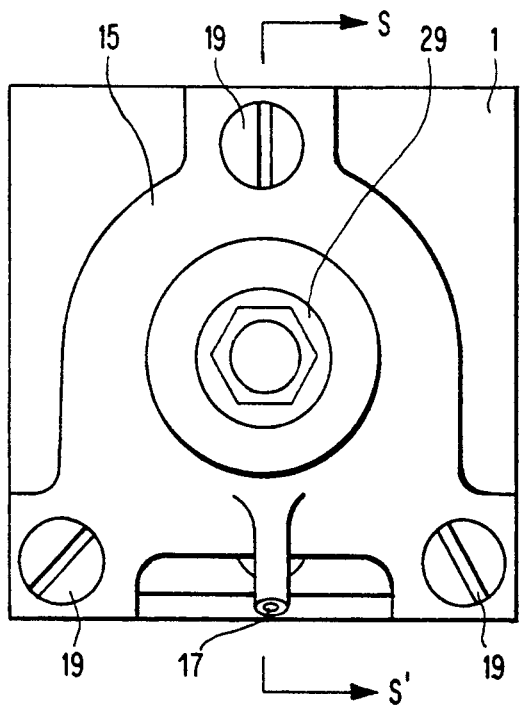

FIGS. 1A and 1B show, a device designed to enable spectroscopic measurements to be made by transmission infrared spectroscopy on gas samples at high temperatures and/or high pressures. The dimensions of such a cell and certain other features can be advantageously determined as taught by GB 2097548 and modified to allow high pressure operation.

FIG. 1A shows a cross-sectional view of such a device while FIG. 1B shows an end view. The device consist of a cell body 1 with gas entrance and exit pipes 2 and 3 communicating with a central axial optical cavity 4 through which the gas is constrained to flow. The ends of cavity 4 are respectively closed by disc-shaped optical windows 5 and 6 which may be supported on the faces of the cavity by optional thin hollow cylinders (hereinafter referred to as a "window cushion") 7 and 8. The outer faces of the optical windows 5 and 6 are supported by seals (for example, o-rings) 9 and 10 which are in turn restrained by hollow screws 11 and 12. The cell is heated by electrical cartridge heater 13 and temperature controlled by means of a thermocouple 14. To provide thermal uniformity, a cover (not shown) and possibly thermal insulation may be added. The device so far described would provide the essentials (suitable mounting arrangements for the cell in the spectrometer can be added, if required, as taught by GB 2097548) of a viable high pressure/high temperature gas cell for spectroscopy. However, at high temperatures, the pressure rating would have to be reduced as a result of the loss in mechanical strength of windows 5 and 6.

Gas tight enclosures 15 and 16, each incorporate at least one gas inlet/outlet pipe 17 and 18 enabling each enclosure to be pressurized. Enclosures 15 and 16 are each attached to the cell body 1 by three screws 19 and 20 illustrated in FIG. 1A and FIG. 1B. A gas tight seal is provided between the cell body 1 and each of the enclosures 15 and 16 by o-rings 21 and 22. Optical windows 23 and 24 are supported between window cushions 25 and 26 and by o-rings 27 and 28 restrained by hollow screws 29 and 30, thereby forming high pressure gas tight window assemblies for enclosures 15 and 16.

The effect of these additions is to form secondary chambers 31 and 32 which can be gas pressurized through pipes 17 and 18 to reduce the pressure differential across windows 5 and 6 preferably to near zero. The pressure limit of the modified cell is then determined solely by high pressure windows 23 and 24 which are operating at an optimal temperature for mechanical strength of the window material. Thermal transfer between the cell body 1 and the added enclosures may conveniently be reduced by profiling the enclosures as shown in FIG. 1B for enclosure 15 or by other appropriate conventional means.

Figure 2A:
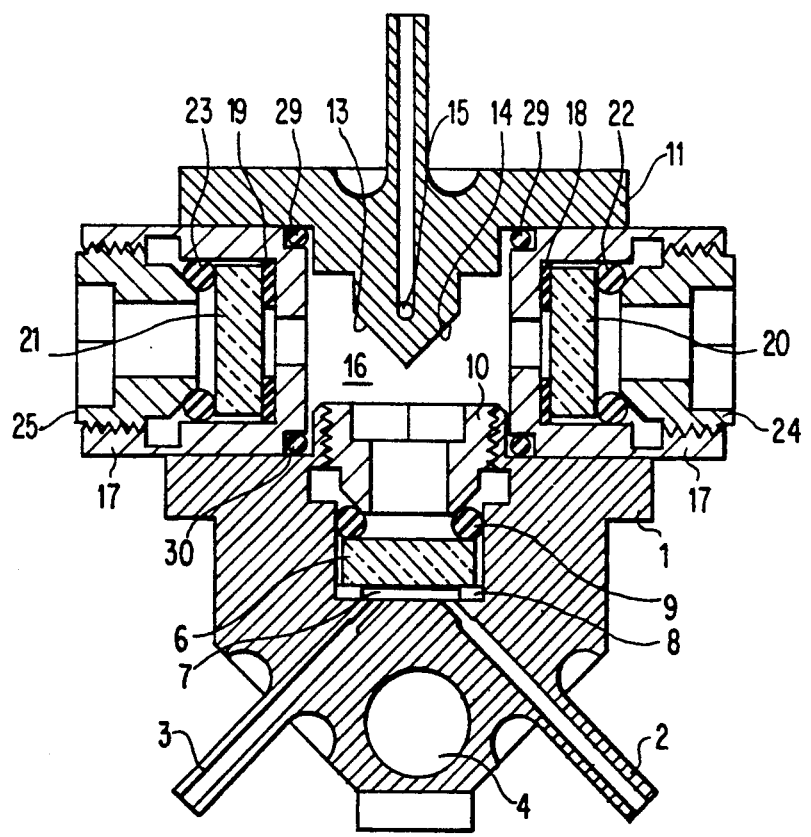
Figure 2B:
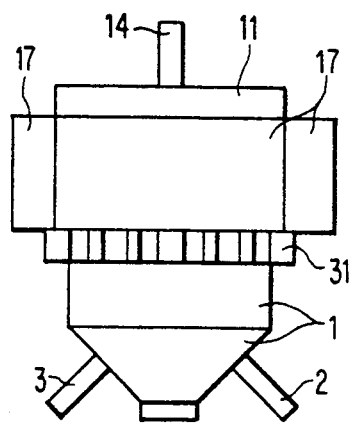
Figure 2C:
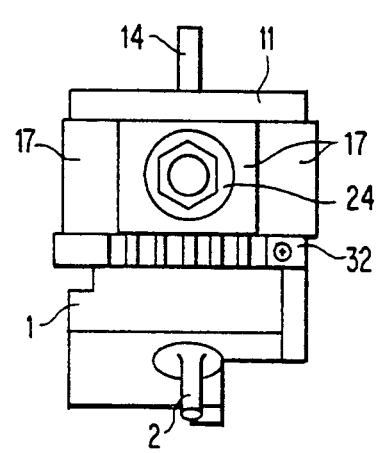
Figure 2D:
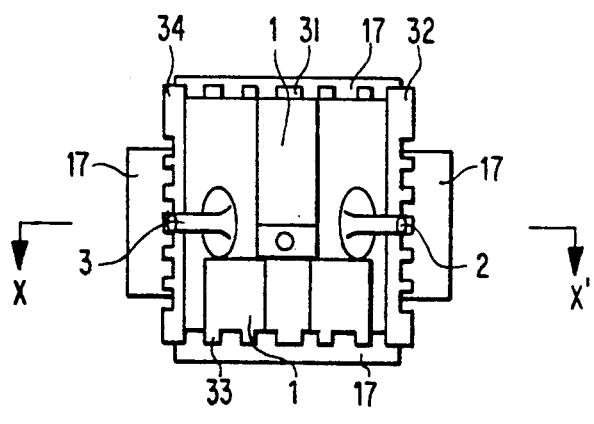

FIGS. 2A, 2B, 2C, 2D and 2E show a second embodiment of a device designed for the spectroscopic examination of fluids (generally liquids or supercritical fluids or strongly absorbing gases) at high pressures and temperatures. U.S. Pat. No. 4,405,235 has taught how a reflectance cell can advantageously be used for such measurements on liquid samples. FIGS. 2A, 2B, 2C, 2D, 2E illustrate how such a cell can be adapted for high pressure/high temperature use and how the present invention can be advantageously incorporated. FIG. 2A shows the device in enlarged cross-section The cell body 1 incorporates two fluid inlet/outlet pipes 2 and 3. The cell is heated by an electrical cartridge heater inserted in cylindrical cavity 4 by means of a sensing thermocouple inserted in cylindrical cavity 5. The fluid entering the cell is contained between optical window 6 and the reflecting backface of the optical cavity 7. This reflecting backface can advantageously be profiled in the cell body 1 as taught by U.S. Pat. No. 4,405,235. The optical pathlength for the cell can be varied by using an appropriate thickness for window spacer 8 (a thin hollow cylinder) so that, for example, no spacer is inserted to give a very short pathlength (the sample is contained within the backface profile) or a spacer of (say) 1.0 mm is used to provide a nominal 2 mm optical pathlength by reflection. A high pressure window seal is formed by 9 (for example, an o-ring) with supporting hollow screw 10. The assembly so far described effectively forms a viable high pressure/high temperature fluids cell by the addition of an optical system to deflect the beam into the cell and return the reflected radiation from the cell to the spectrometer. In the case illustrated herein, such an optical system is incorporated into the design and shown as item 11 in FIG. 2A with angled reflecting optical faces 12 and 13.

Figure 2E:
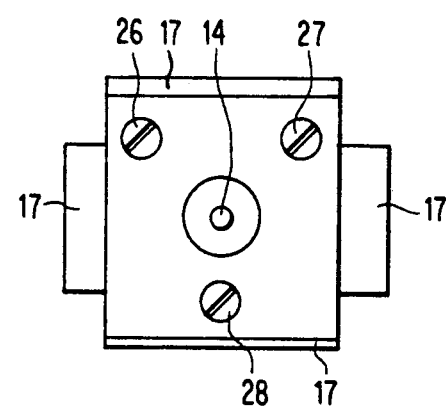

Optical system 11 is designed to contain at least one gas inlet/outlet pipe 14 which communicates through cross-hole 15 with the secondary gas pressurized chamber 16. Chamber 16 is in part enclosed by 17, which serves to correctly space the angled reflecting optical faces 12 and 13 from the cell cavity 7 and also to incorporate two high pressure window assemblies; these window assemblies consist of optional window cushions 18 and 19, secondary high pressure windows 20 and 21 with gas tight seals (for example, o-rings) 22 and 23 supported by hollow screws 24 and 25. Cell body 1, enclosure 17 and optical system 11 are attached by means of three screws 26, 27, 28 (as shown in FIG. 2E) threaded into the face of cell body 1; the gas tight seal for secondary chamber 16 being provided by means of o-rings 29 and 30 as shown in FIG. 2A. Thermal transfer from the heated cell to the enclosure 17 can be conveniently reduced by removing excessive material from 17 or by other conventional methods; thermal uniformity of cell body 1 can be improved by adding a cover (not shown) mounted on castellated edges 31, 32, 33, 34 (FIG. 2D) to enclose body 1 or by other conventional methods.

By admitting a gas through pipe 14 into secondary chamber 16 so that the pressure of the gas corresponds to the pressure of the sample fluid in cavity 7, the pressure differential across window 6 is reduced to near zero. The pressure limiting factor in the system then becomes windows 20 and 21 where the window materials are operating at near optimal temperatures. It will be appreciated that whereas two secondary windows have been incorporated into this design (for convenience), it would also be possible to design for use of only one secondary window by housing the optical reflecting surfaces 12 and 13 outside the secondary chamber.

Certain general advantages arise in relation to the invention and are illustrated by the two above embodiments of the invention. Since the pressure differential across the primary (inner window) is reduced preferably to near zero, by application of this invention, a much thinner window may then be used if desired. Also, a wider choice of materials is available for the primary window(s) as this window is no longer required to have any significant high pressure capability. Again, although the two embodiments illustrated here are shown with conventional high pressure window seals for the primary window(s), because the pressure across the window is now near zero, alternative window sealing methods (simpler) and sealing materials may be used. The modified requirements for the sealing materials and sealing methods may allow higher operational temperatures to be achieved than would otherwise be possible in the absence of this invention. Sealing material used may be chosen for characteristics at very high temperature rather than ability to withstand high pressure. With the choice of window material and seal material not limited by pressure a whole new area of research may open up. The invention also allows the use of a gas pressure in the secondary enclosure which is higher than the pressure of the fluid contained by the primary window; this may be advantageous when certain types of sealing method are used for the primary window. While in the two examples put forward here to illustrate the embodiments of the invention, the primary optical elements are conventional disc windows, the invention may be beneficially applied to any element which transmits radiation and which is required to contain a fluid. In the case of flowing samples or other situations where the pressure is variable as a function of time, it will be appreciated that a simple gas pressure control system can be used to provide corresponding pressure variations for the secondary gas chamber pressure so that the pressure differential across the primary optical element is maintained at near zero or as otherwise desired. In the examples given, one gas pressurization inlet/outlet pipe has been shown for each secondary gas pressurization chamber, but in certain cases it may be desirable to provide more than one such inlet/outlet pipe per secondary chamber.

Claim:

1. A method of reducing the pressure differential across a primary optical element of a fluid containment vessel having a cavity therein partially defined by said optical element for receiving a sample, said cavity being subjected to a predetermined pressure, comprising the following steps:

providing an external gas pressurizable enclosure adjacent an exterior of said optical element; and pressurizing said enclosure to a pressure approaching said predetermined pressure so as to minimize the pressure differential across said optical element.

2. The method of claim 1, wherein said pressurizing step includes the step of pressurizing said enclosure to a pressure substantially equal to said predetermined pressure so that the pressure differential across said optical element is substantially zero.

3. The method of claim 1, wherein said pressurizing step includes the step of pressurizing said enclosure to a pressure substantially greater than said predetermined pressure.

4. A device for enabling spectroscopic examination, comprising:
a cell body having a cavity therein;
a first optical element secured to said cell body and partially defining said cavity, said cavity being on an internal side of said first optical element;
means for introducing gas into a removing gas from said cavity so as to pressurize said cavity to a predetermined pressure; and
means for pressurizing an external side of said first optical element so as to reduce the pressure differential across said first optical element, said pressurizing means including a second optical element.

5. The device of claim 4, wherein said pressurizing means includes an enclosure on said external side of said first optical element and means for pressurizing said enclosure.

6. The device of claim 4, further comprising means for heating said cell body and for controlling a temperature thereof.

7. The device of claim 4, wherein said first optical element is disposed transversely with respect to said second optical element.

8. The device of claim 7, further comprising reflecting means for reflecting light from said first optical element to said second optical element.

9. A means for supporting a primary radiation-transmitting element which is subject to high temperatures and high pressures, comprising a secondary enclosure for containing a pressurized gas atmosphere and which incorporates a secondary radiation-transmitting element, wherein the primary radiation-transmitting element experiences a reduced pressure differential.

* * * * *

UNITED STATES PATENT AND TRADEMARK OFFICE
CERTIFICATE OF CORRECTION

PATENT NO. : 5,223,716

DATED : June 29, 1993

INVENTOR(S) : Valentine J. Rossiter

It is certified that error appears in the above-identified patent and that said Letters Patent is hereby corrected as shown below:

Column 1, line 53, change "t" to --to--.

Column 5, line 19, change "a" to --and--.

Signed and Sealed this

Twenty-sixth Day of July, 1994

Attest:

BRUCE LEHMAN

*Attesting Officer*          *Commissioner of Patents and Trademarks*